(12) United States Patent
Gilbert

(10) Patent No.: US 6,338,282 B1
(45) Date of Patent: Jan. 15, 2002

(54) PORTABLE LIQUID SAMPLING SYSTEM

(75) Inventor: Richard Gene Gilbert, Littleton, CO (US)

(73) Assignee: Agro-Enviro Consultants, Inc.

( * ) Notice: Subject to any disclaimer, the term of this patent is extended or adjusted under 35 U.S.C. 154(b) by 0 days.

(21) Appl. No.: 09/426,796

(22) Filed: Oct. 22, 1999

Related U.S. Application Data

(63) Continuation of application No. 09/100,449, filed on Jun. 19, 1998, now abandoned.

(51) Int. Cl.[7] .................................................. G01N 1/14
(52) U.S. Cl. .................................. 73/864.34; 73/864.73
(58) Field of Search ........................ 73/804.34, 864.73

(56) References Cited

U.S. PATENT DOCUMENTS

| | | | |
|---|---|---|---|
| 2,388,548 A | 11/1945 | Jurs ............................. | 137/18 |
| 2,836,068 A | 5/1958 | Clift ............................ | 73/421 |
| 2,841,012 A | 7/1958 | Romer ......................... | 73/421 |
| 3,841,156 A | 10/1974 | Wolfe .......................... | 73/291 |
| 3,901,084 A | 8/1975 | Breilsford .................... | 73/421 |
| 3,924,471 A | 12/1975 | Singer .......................... | 73/421 |
| 4,462,265 A | 7/1984 | Rein ........................ | 73/863.33 |
| 4,606,233 A | 8/1986 | Burney .................... | 73/864.63 |
| 4,669,321 A | 6/1987 | Meyer ..................... | 73/863.85 |
| 4,683,761 A | 8/1987 | Stock ...................... | 73/864.34 |
| 4,754,654 A | 7/1988 | Johnson ................... | 73/864.34 |
| 4,949,582 A | 8/1990 | Vollweiler ............... | 73/804.63 |
| 5,113,711 A | 5/1992 | Davloor .................. | 73/864.63 |
| 5,167,802 A | 12/1992 | Sandstrom ................. | 210/134 |
| 5,197,340 A | 3/1993 | Jones ...................... | 73/864.35 |
| 5,237,878 A | 8/1993 | Hackenberg ............. | 73/864.34 |
| 5,386,735 A | 2/1995 | Langdon .................. | 73/863.23 |
| 5,390,553 A | 2/1995 | Lynn ....................... | 73/864.63 |
| 5,437,201 A | 8/1995 | Krueger ................... | 73/864.35 |
| 5,441,071 A | 8/1995 | Doherty ...................... | 137/15 |
| 5,442,970 A | 8/1995 | Hutchins .................. | 73/864.63 |

(List continued on next page.)

OTHER PUBLICATIONS

Gilbert, et al "A Simple Tube–Type Water Profile Sampler," Water Resources Research, vol. 12, No. 4, Aug. 1976, pp. 812–815.

A. Daigger & Company, Inc., "Laboratory Equipment and Supplies," 1996, pp. 293 and 297.

Hach, "Products for Analysis," 1998, pp. 105, 151, 183, 189, 263, 290, 315, 335.

Forestry Suppliers, Inc., "1996 Educational Products," pp. E23 and E33.

(List continued on next page.)

*Primary Examiner*—Thomas P. Noland
(74) *Attorney, Agent, or Firm*—Holme Roberts & Owen, LLP

(57) ABSTRACT

The invention provides a liquid sampling device and method using a chamber in which a vacuum is created to draw a liquid sample through a sample intake tube assembly into a sample receptacle placed in the chamber. The vacuum is created by a vacuum pump attached to an entry port in the chamber. The sample intake tube assembly is inserted through a second entry port in the chamber. One end of the sample intake tube assembly is placed in the open sample receptacle located in the chamber, while the other end is placed in the sample site. The independence of the sample intake tube assembly and the vacuum pump stem promotes sample purity. The sample intake tube assembly has a flexible collar which is inserted into and creates a seal with the entry port of the chamber. After a sample is taken and the vacuum pump disengaged, the sample intake tube assembly and its collar may be removed and replaced by a new tube assembly and collar, so minimizing the risk of microbial and chemical cross-contamination of samples by repeated use of the same intake tube assembly.

14 Claims, 5 Drawing Sheets

U.S. PATENT DOCUMENTS 5,463,909 A    11/1995  Eldridge ................... 73/864.52
5,686,673 A    11/1997  Kabis ....................... 73/863.31
5,943,440 A *  8/1999   Douley et al. ........... 73/804.73

OTHER PUBLICATIONS

Forestry Suppliers, Inc., "1997 Educational Products," pp. 211–217, 258–262.

* cited by examiner

PORTABLE LIQUID SAMPLING SYSTEM

CROSS-REFERENCE TO OTHER APPLICATIONS

The present invention is a continuation of a copending non-provisional application having application Ser. No. 09/100,449 and filing date Jun. 19, 1998 and now abandoned, and the title "Portable Liquid Sampling System."

FIELD OF THE INVENTION

The present invention relates generally to methods for sampling liquids and, in particular, to a liquid sampling system that minimizes sample cross-contamination and is also portable and adaptable for use in extreme climatic conditions and challenging physical environments. The invention is particularly advantageous for use in the field, where the user desires to collect multiple samples in succession, without contamination of latter samples by previous ones. The invention provides advantages in collecting samples from sites located underground or in difficult terrain, or where the user desires to avoid contact with the sample liquid. Because the invention uses a vacuum pump to draw samples, it also is advantageous where the user desires to collect large field samples, in excess of 500 milliliters in volume.

BACKGROUND OF THE INVENTION

A variety of liquid sampling devices and methods have been developed for use in the laboratory and field. Only a few of these have been designed specifically to address the problem of sample contamination. A common contamination problem is cross-contamination of samples. This occurs when a sample device's collecting tube or vessel is used repeatedly, without cleansing, to collect multiple samples. Each of the samples taken may leave liquid droplets or residue on the walls of the sample collecting tube or vessel. The latter samples taken are then contaminated by droplets or residue left in the tube and vessel by previous samples. This problem can be especially challenging in the field, where there usually is no access to washing facilities and autoclaves, as there might be in the laboratory. Field methods of flushing or purging the intake tube or receptacle with distilled water or other solvents, or with a burst of air or inert gas, often do not completely remove droplets or residue that may adhere to the walls of the collecting tube or vessel and contaminate later samples. Such droplets and residue can introduce substantial error in sampling results, especially when samples are collected for microbial analysis or analysis of relatively low levels of chemical pollutants. Field devices that are designed to address the issue of sample contamination, such as the cup and rod, grab bag, ampule, and cylinder samplers, can be awkward to use in challenging environments. Each of these requires the user to lift or pull the sampling device, containing the collected sample, out of the sample site to the user's work area. The cup and rod sampler, for example, consists of a long rod to which is attached a cup for collecting samples. The user must grasp the rod by its handle and dip the cup into the body of liquid to be sampled. Once he has collected a sample in the cup, he must lift the cup out of the sample site and pivot it around to his work are With a cylinder sampler, the user lowers a cylindrical sampling device into the body of liquid to be sampled by means of a cord or cable attached to the sampling device. Once the sample is captured, the user raises the cylinder to the surface by pulling the cord or cable. With these types of sample devices, the user generally supplies the power for collecting the sample, and the size of the sample collected can be limited by the strength and stamina of the user. In addition, because of their shape and size, these devices are often difficult to use with certain sample souses, such as underground aquifers, storage tanks, ponds and streams in winter conditions (wholly or partially covered by ice), hot springs, septic and waste water tanks and lagoons and the lower strata of large bodies of water. Moreover, the method for avoiding sample contamination usually requires the user manually to remove a sample receptacle from a sampling device covered with the liquid sampled, exposing the user to contact with the liquid sampled. This can be awkward in the best of conditions, and especially in sub-freezing conditions or where the sample site is extremely hot, but also can be unpleasant and create a health risk for the user when the liquid sampled contains toxic chemicals or bacteria.

SUMMARY OF THE INVENTION

The present invention provides a system for collecting liquid samples in the field, using a vacuum pump to draw the liquid from the sample site through a hollow sample intake tube to the sample receptacle. An important feature of the invention is the independence of the vacuum pump system and the sample intake tubing. This is accomplished by use of a vacuum chamber with separate entry ports for these two functions, one entry port furnishing a connection to the vacuum pump system and the other providing access to the sample intake tubing. Once the sample intake tubing is inserted into the chamber, the intake tubing is then further inserted into an open sample receptacle placed within the chamber. When the chamber is closed and the vacuum pump engaged, air is drawn out of the vacuum chamber and the open sample receptacle within it, creating a partial vacuum that also draws liquid sample through the sample intake tube and into the sample receptacle. The chamber is preferably either made of transparent material or has a window which permits observation of the level of liquid in the sample receptacle. Once the desired quantity of liquid is collected in the sample receptacle, the vacuum pump is disengaged, and the chamber may be opened to allow removal of the sample receptacle for storage and transport to the laboratory, and placement of a new sample receptacle in the chamber. Also, the sample intake tubing can be removed and replaced with a new piece of intake tubing, so preventing contamination of the next sample by the one just taken. Used sample intake tubing can either be disposed, or saved and returned to the laboratory for cleansing. It is to be appreciated that this method avoids filling the vacuum chamber with, or immersing the sample receptacle in, sample liquid, so that the user can remove, replace and store sample receptacles without coming into contact with the sample liquid.

The use of hollow tubing, of whatever length and diameter desired to draw the sample, and vacuum power to transport the sample liquid to the sample receptacle, makes the invention highly versatile in the field. The intake tubing, particularly if fitted with rigid tubing on the sample collection end, can be inserted or directed through narrow openings in ice, vegetation, soil, or rock layers to gain access to liquid sample sites under frozen ponds or streams, in bogs or marshes, or underground. Hollow tubing also is very adaptable to insertion in narrow access pipes or tubes to storage tanks, and septic and sewage systems. It can be cut in long lengths and weighted and tossed across or into hot springs and geyser pools, fast running streams, and open sewage and wastewater lagoons. It can be attached to a rod or dowel to facilitate precise placement of the sample collection end into a particular area of a body of sample liquid. Further, the use of a vacuum pump system provides the power to draw the liquid sample up from a sample site located at an elevation much lower than the sample receptacle. The vacuum pump system also provides the capacity to draw numerous samples in succession, or a single large sample.

Because the vacuum chamber and vacuum pump system do not come in contact with the liquid sample, they may be constructed of lightweight materials such as plastic. Moreover, the vacuum pump system can be powered either manually by a hand pump, such as those readily available in the market, or by a small battery, such as a 12 volt battery used in motorcycles. These features of the system and use of lightweight hollow tubing for collecting samples make the invention, in many of its applications, highly portable, which enhances its advantage when used in field work, especially on ecological projects in wilderness and other difficult terrain.

The invention thus provides a system for obtaining liquid samples without cross-contamination of samples, and enhances the user's capacity to collect samples of various sizes in challenging physical environments with reduced physical effort and lowered risk that the sample liquid will contact the user's skin or clothing.

BRIEF DESCRIPTION OF THE DRAWINGS

For a more complete understanding of the present invention and further advantages thereof reference is now made to the following Detailed Description taken in conjunction with the drawings, in which.

DETAILED DESCRIPTION OF THE PREFERRED EMBODIMENT

The present invention discloses a device and method for taking liquid samples in the field that minimize cross-contamination of samples, and provide enhanced versatility and portability in challenging environments, and improved capacity to collect successive a small and/or large volume samples. Examples of applications where such a system would have particular advantages include projects for sampling underground bodies of water, sampling projects undertaken in winter conditions, sampling performed in wilderness or back country stream and marshes, sampling from hot springs and other geothermal sources, and sampling of underground storage tanks, septic systems and wastewater lagoons. What follows is a description of one such application of the invention: a project that involves taking liquid samples from an underground aquifer accessed by a narrow pipe extending from the soil surface to the aquifer. It should be appreciated that the system and method for liquid sampling involved in the present invention is not limited to any such particular application.

Figure 1:
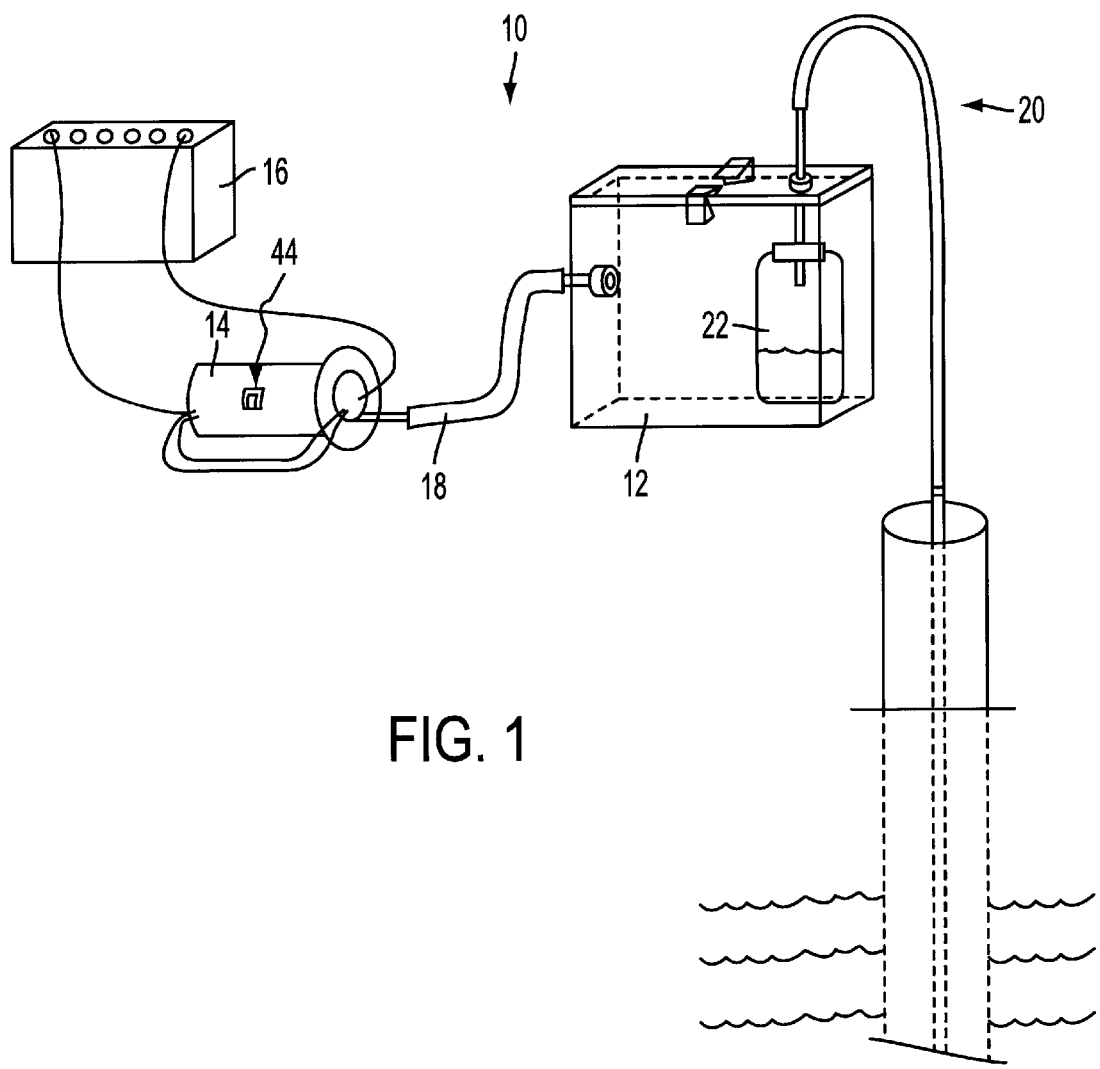
FIG. 1 generally depicts the main components of the liquid sampling system.

Referring to FIG. 1, a liquid sampling device 10 in accordance with the present invention includes in one embodiment, several main components, that are connected when the device 10 is in operation, but that may be detached for transport to and from the sample site. These are a vacuum chamber 12, vacuum pump 14, battery 16, vacuum pump tubing 18, and sample intake tube assembly 20. It is to be appreciated that the capacity of these components to be detached for transport, and then reconnected, enhances the portability of the device 10.

As noted, the invention uses a chamber 12 in which a vacuum, i.e., a subambient pressure, is created. The chamber 12 is constructed of a material that will not collapse when a vacuum is established in the chamber, such as plexiglass or other hard plastic. Any joints, entry ports, windows, etc., in the chamber 12 are well sealed, so that the vacuum will be maintained as needed, and impurities will not be drawn into the chamber 12 through any openings other than the desired access ports. In the illustrated embodiment, a box-shaped chamber 12 is used, which provides the advantage that the chamber 12 may then be placed in a stable position on the ground or the user's work area In another embodiment of the chamber illustrated in FIG. 4, a molded plastic cylinder or bottle could be used as a vacuum chamber, so reducing the number of joints that must be sealed to preserve the vacuum in the chamber.

Although a sample may be directly collected in the vacuum chamber 12, the illustrated embodiment of the invention contemplates that the user will manually place one or more sample receptacles 22 in the chamber 12 so as to reduce cleaning and the risk of cross contamination. The chamber 12 is therefore of a size larger than the sample receptacle(s) 22 to be used. For most field applications, and in the illustrated embodiment, a vacuum chamber 12 with a volume of one to two gallons would be sufficient, although smaller or larger chambers could be used for various field and industrial applications where smaller or larger samples are required. The one-to-two gallon size is adequate to accommodate several 200-500 milliliter sample receptacles, which enables the user to take several samples in rapid succession, but still is of a size that makes the invention highly portable to back country locations.

Figure 2:
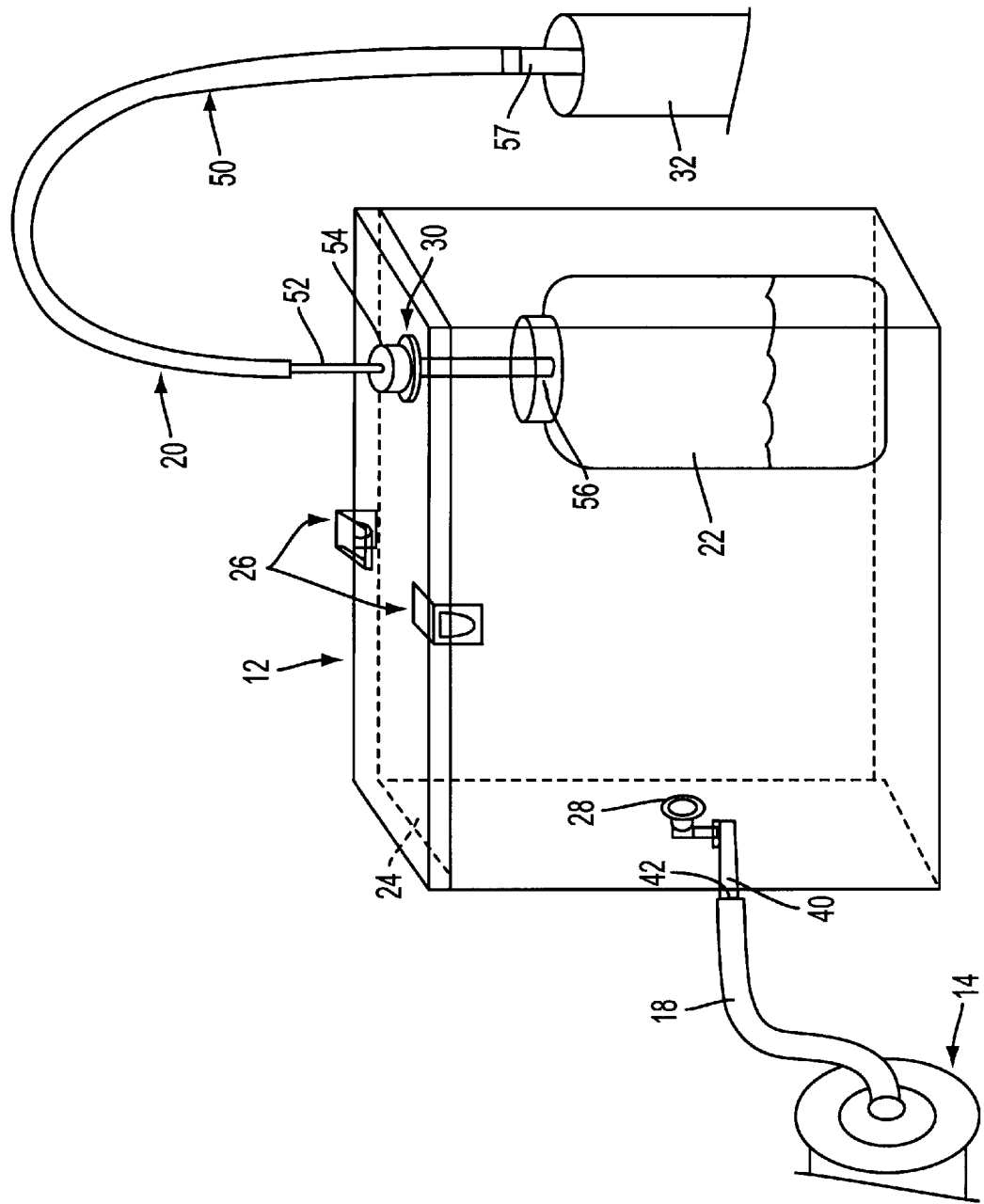
FIG. 2 provides an enlarged view of the vacuum chamber.

Referring to the enlarged view provided in FIG. 2, the chamber 12 has three access ports. First, it has a cover or door 24 that can be easily opened and closed to admit and remove sample receptacles, and that when closed is sealed to maintain a vacuum within the chamber 12 when the device 10 is in operation. The door 24 can be one of the panels forming the chamber 12, or a portion thereof, and can be hinged to, detachable from or otherwise operable to selectively enclose or allow access to the interior of chamber 12. In the illustrated embodiment, the door 24 is the top lid of the chamber 12. The area where the door contacts the side walls is preferably lined with a sealing material such as an o-ring or elastomeric gasket, which assists in creating an airtight seal when the vacuum pump is activated. The door 24 is preferably latched to the chamber side walls so as to facilitate initiation of a vacuum in the chamber 12. The door 24 and two of the side walls of the illustrated embodiment are fitted with latches 26 that when closed pull the door tightly against the side walls, so providing a vacuum seal. In addition to the door 24, the chamber 12 also has two smaller entry ports 28 and 30, one port 28 to accommodate the hollow tubing 18 connecting the chamber 12 to the vacuum pump system 14, and the other 30 to accommodate the sample intake tube assembly 20, through which will flow sample liquid from the sample source 32 when the device 10 is in operation. In the illustrated embodiment, the entry port 28 connecting to the vacuum system 14 is located in a side wall of the chamber 12. In addition, the port 30, which permits access to the sample intake tube assembly 20, is located in the door 24. It will be appreciated that tubing 18 and intake tube assembly 20 may each include multiple conduits, joints and other elements defining an appropriate flow pathway. Each of the entry ports is sealed by an appropriate sealing material such as an elastomeric o-ring, gasket, or pressure-friction tube connection.

The device 10 involves a system for creating a vacuum in the chamber 12. In the illustrated embodiment of the invention, the vacuum is created in the chamber 12 through a vacuum pump 14 connected to the chamber 12 through flexible hollow tubing 18 releasably attached to the entry port 28 located in a side wall of the chamber 12. The flexible tubing 18 is attached to a short length of rigid tubing 40 fitted with a tubing coupler or other function tubing connection at the pump tube end 42, that tightly holds the flexible tubing 18 when the system is in operation, but also permits easy detachment of the tubing 18. Also, in other embodiments, especially in which the size and shape of the chamber 12 and pump 14 are different, the entry port 28 may be located on another wall, or on the door 24.

There are a variety of small vacuum pumps on the market that would be suitable for use with the invention, including a number of hand-operated pumps. In the illustrated embodiment of the invention depicted in FIG. 1, the vacuum pump 14 is an electric pump powered by a battery 16, such as a small (12 volt) motorcycle battery. When an electric pump 14 is used, the sampling device 10 may have greater power than a hand-powered pump, allowing larger samples to be collected, as well as multiple samples in rapid succession. In addition, the use of an electric pump 14 combined with a battery 16 of an appropriate size makes the device 10 both portable and versatile in difficult environments.

Figure 3:
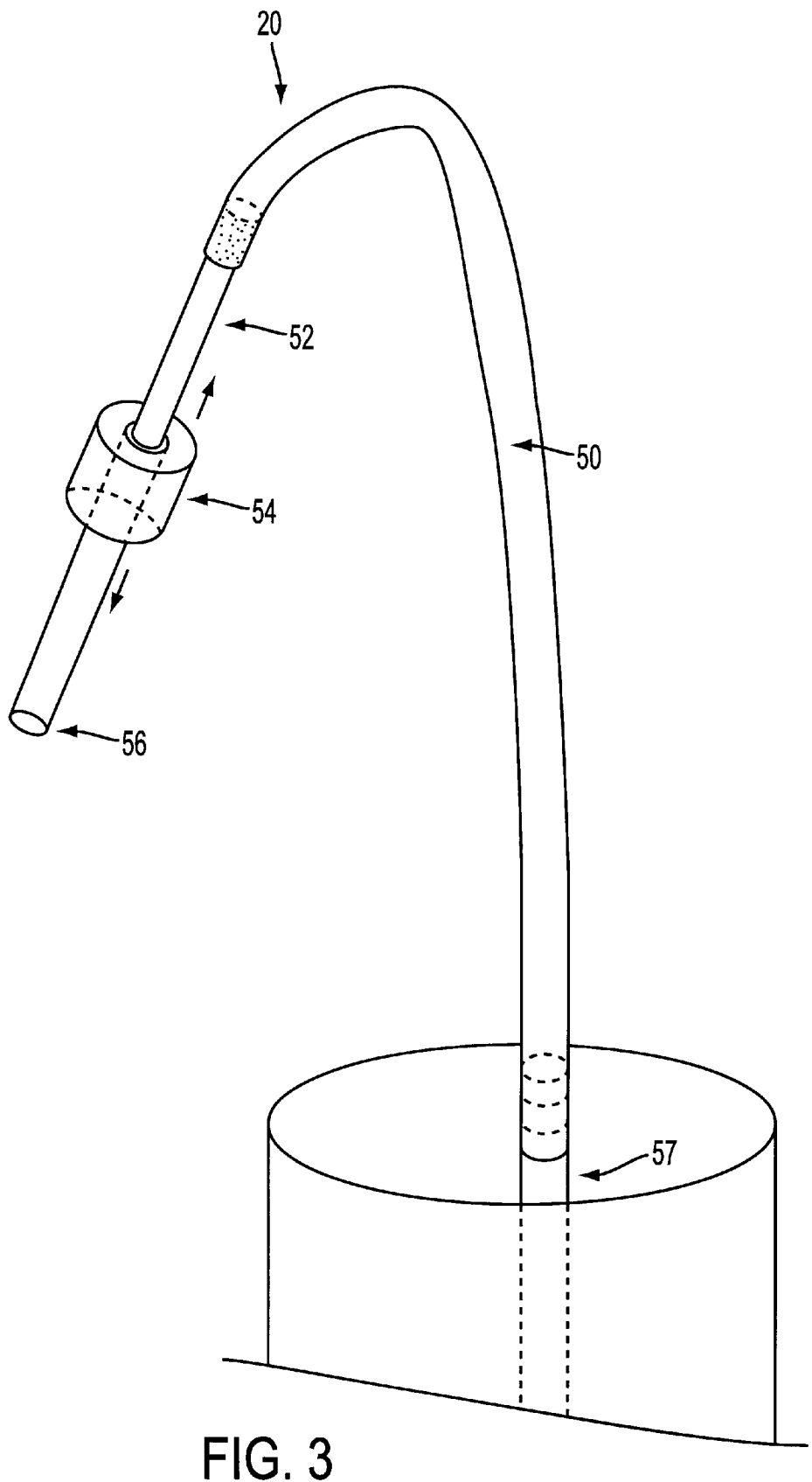
FIG. 3 provides an enlarged view of the sample intake tube assembly.

The invention also involves a sample intake tube assembly 20 for drawing the sample into the sample receptacle 22. An enlarged view of the sample intake tube assembly is found in FIG. 3. A preferred feature of the invention is the independence of the sample taking components from the vacuum components. The components of the sample intake tube assembly 20 include, first, the hollow sample intake tubing 50, one end of which is placed in the sample source 32, i.e., the body of liquid to be sampled. The other end of the tubing 50 is inserted into the vacuum chamber 12. In the illustrated embodiment, the sample intake tubing 50 is made of flexible plastic tubing, such as Tygon tubing. Attached to the chamber end of the illustrated tubing 50 is a short length (e.g., five to ten inches) of rigid hollow tubing 52, made of a material such as plastic or glass, which facilitates insertion into the entry port 30 to the chamber 12. Attached to the sample collection end of the tubing 50 is rigid hollow tubing 57, sized to facilitate insertion into the sample source 32.

Referring to FIG. 2, and as noted above, in the preferred embodiment, the entry port 30 is located on the door 24, or top lid, of the vacuum chamber 12. This permits the rigid sample intake tubing 52 to be inserted downwards through entry port 30 into the chamber 12, and then into or over the opening of the sample receptacle 22 placed within the chamber 12. The rigid tubing 52 of the sample intake tube assembly 20 is fitted with a vacuum sealing stopper or collar 54 at the point where the rigid sample intake tube 52 enters the port 30 to the chamber 12. The collar 54 is tapered slightly in the direction of the chamber 12 (i.e., narrows as it extends into port 30) and is manufactured of flexible, soft material, which will compress and be drawn slightly into the entry port 30 as pressure is lowered in the chamber 12 by the vacuum pump 14, until it vacuum-seals the entry port 30. In one embodiment of the invention, the collar 54 may resemble a single-hole rubber postioned on the rigid hollow tubing 52 prior to insertion in the entry port 30 of the chamber 12.

The use of a collar 54, positioned on the rigid hollow tubing as an element of the sample intake tube assembly 20, and functioning to seal the entry port 30, promotes sample purity. An alternate approach, in which the collar is permanently affixed to the entry port 30 and the rigid hollow tubing 52 must be inserted through the collar 54 on each use, would increase the risk of sample contamination. With this alternate approach, sample contamination could occur as follows. If the rigid hollow tubing 52 were pulled back out through the collar 54 after a sample is taken, liquid sample droplets clinging to the sample receptacle end 56 of the tubing 52 might brush off and adhere to the interior of the collar 54. When a fresh length of tubing 52 is inserted through the collar 54 into the chamber, the sample receptacle end 56 of the tubing 52 might then be contaminated by droplets from the previous sample. In the illustrated embodiment, when the vacuum system is in operation, the collar 54 is drawn into and seals the entry port 30, but is removed with the sample intake tubing 52 after each use, so that the sample receptacle end of the tubing 56 avoids contact with and does not contaminate the entry port 30.

In the illustrated embodiment, the device 10 involves also a mechanism for controlling the amount of sample to be collected This involves a switch 44 for activating and deactivating the vacuum pump, and a method/structure by which the vacuum pump can be deactivated or disengaged from tubing 18 and/or chamber 12 when the amount of sample volume is at the desired level in the sample receptacle 22. If desired, such operation may be controlled automatically in response to signals from a float valve associated with receptacle 22, a strain gauge associated with a receptacle support, a flow meter associated with tubing 50, a timing system or any other subsystem for providing feedback or an indication concerning the sample. In the illustrated embodiment of the invention as depicted in FIG. 1, the mechanism for controlling the intake of sample involves the following elements: an on/off switch 44 is connected to the vacuum pump 14 and is readily accessible to the operator, the sample receptacle 22 is clear or transparent; and all or a part of the vacuum chamber 12 is constructed of a transparent material such that the operator can see the level of sample liquid in the receptacle 22 and, once the device 10 is operational can deactivate the switch 44 to stop the flow of sample liquid into the receptacle 22. In other embodiments of the invention, sensing means such as noted above may be connected to the vacuum pump 14, so that when the amount of sample liquid in the receptacle 22 reaches the desired level, or the desired amount of sampling has otherwise been conducted, the pump 14 will automatically switch off.

The method of using the illustrated embodiment preferably involves, first, opening the door 24 of the vacuum chamber 12 and placing an open sample receptacle 22 into the chamber 12. The door 24 of the chamber 12 is closed with vacuum-latches 26. The rigid sample receptacle end 56 of the sample intake tube assembly 20 is inserted in the open top of the sample receptacle 22 and the collar 54 fitted into the entry port 30. The rigid sample collection end 57 of the sample intake tubing 50 is then directed down a narrow pipe 32 into the underground aquifer. Through previous testing, the user is familiar with the distance from the top of the pipe 32 to the liquid sample, and the length of tubing 50 and rigid sample collection end 57 necessary to reach the desired depth within the aquifer. The use of the rigid sample collection end 57 permits the user to direct the sample intake tubing 50 into the pipe 32, or other narrow opening to the sample source, with minimal contact with and disruption of any residue on the walls that might in turn adhere to the sample collection end 57 or dislodge and fall into the sample source, so causing sample contamination. Prior to the activation of the vacuum pump system 14, the air pressure in the inverted hollow intake tubing will prevent liquid at the upper levels of the aquifer from entering the tubing 50. Only when the vacuum pump 14 is activated will liquid sample enter and be drawn into the intake tubing 50. This feature of the invention enables the user to lower the intake tubing 50 and sample collection end 57 to a desired level, and take samples there, without contamination from upper levels of the aquifer. Once the tubing has been inserted to the desired level, the user activates the on/off switch 44 on the vacuum pump 14. The pump 14 removes air from the vacuum chamber 12, the open sample receptacle 22, and the sample intake the assembly 20, creating a vacuum that then draws liquid sample through the intake tubing 50 and rigid hollow tubing 52 and into the sample receptacle 22. As the liquid sample fills the sample receptacle 22, the user monitors its level through the transparent walls of the chamber 12 and sample receptacle 22, and deactivates the on/off switch 44 when a desired sample amount is collected. Once the vacuum pump 14 is disengaged, the door 24 of the vacuum chamber 12 maybe opened, and the sample receptacle 22 removed and replaced with a clean receptacle. In addition, the sample intake tube assembly 20 is then removed by first grasping the collar 54 and pulling the collar 54 away from the entry port 30 to remove the rigid tubing 52 out through the entry port 30 without allowing any part of the tubing 52 to contact and contaminate the walls of the entry port 30. The assembly 20 may then be replaced with a fresh assembly. It is to be appreciated that intake tubing of the kind described above is relatively inexpensive. It may be disposed, or returned to the laboratory for thorough cleansing. It is also to be appreciated that the sample liquid flows from the sample intake tube assembly 20 to the interior of the sample receptacle 22; no part of the interior of the vacuum chamber 12, or the entry port 30, or the exterior of the sample receptacle 22, becomes coated with sample liquid during the sampling process. The invention provides the advantage that in handling the chamber 12, sample receptacles 22, and the sample receptacle end 56 of the sample intake tube assembly 20 by grasping the collar 54 according to the method described above, the user avoids contact with the sample liquid.

Figure 5:
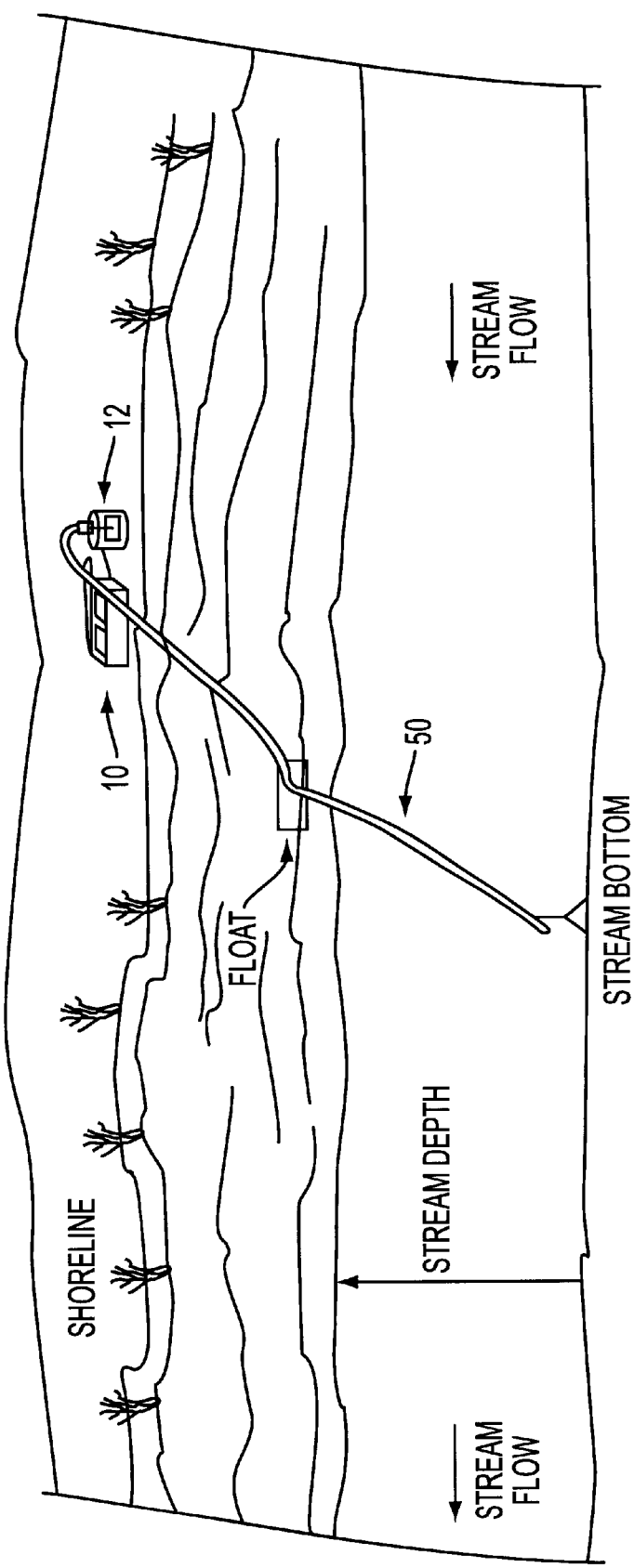
FIG. 5 depicts use of the invention in an application in the field.

Applications of the invention for use in various environments include modifying the length of the sample intake tubing 50 and the power of the vacuum pump 14. A long sample intake tube 50 can be used in combination with a relatively powerful pump when it is desired to take samples from the bottom of deep bodies of fluid, including septic tanks, industrial storage tanks, and underground aquifers of water. In addition, as illustrated in FIG. 5, a long sample intake tube 50 can be used in combination with a float and weight system to take samples at varying surface levels far from shore of a stream, pond or lake or other body of liquid, where the temperature and/or composition of the liquid, current, or the presence of steam or fumes above the liquid, prevents the use of a boat, telescoping rod, or other traditional field methods of taking the sample.

Also, in sub-freezing conditions, the chamber 12 and the portion of the sample intake tubing 50 exposed to the air may be wrapped with insulating material to prevent the sample from freezing. The fact that sample liquid is confined to the interior of the sample receptacle 22 and intake tubing 50 also offers the user advantages in winter conditions—he/she does not have to deal with freezing liquid coating hands or gloves.

In the illustrated embodiment of the invention, the sample intake tubing 50 is made of flexible tubing, having sufficient strength to avoid collapse when a vacuum is created, and of low-cost material such that the intake tubing and attached collar are disposable. In addition, the sample intake tubing 50, rigid tubing 52 and 57, and collar 54 may have the additional characteristic that they can be autoclaved or will tolerate other cleansing methods, such that the used intake tubing assembly 20 can be returned to the laboratory for cleansing before another use.

Figure 4:
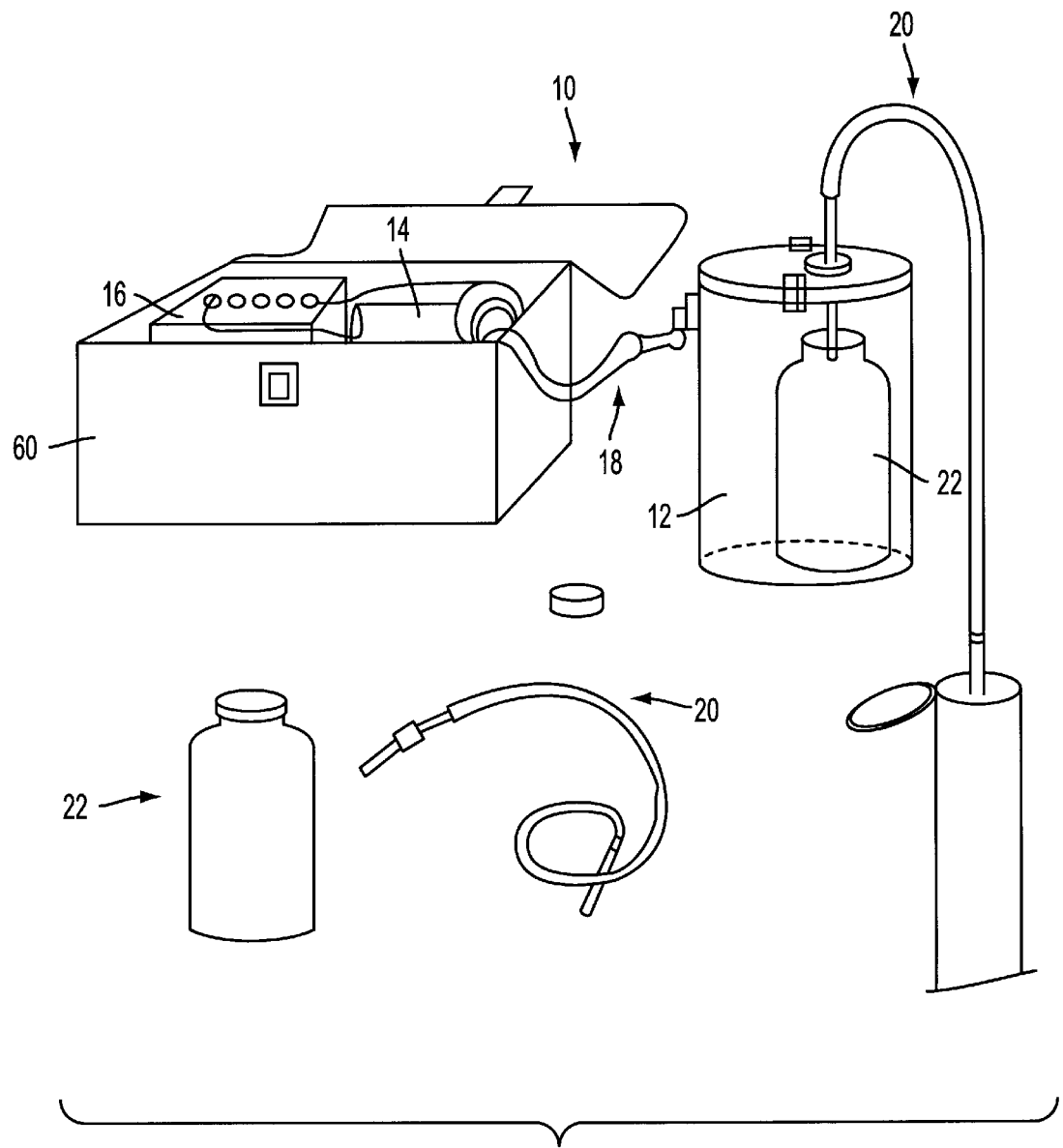
FIG. 4 demonstrates a highly portable implementation of the invention.

As illustrated in FIG. 4, the sampling device 10 can be highly portable. The battery 16 and pump 14 can be housed and carried in a lightweight carrying case, such as a tool box 60. The tool box 60 can be opened and the battery 16 and pump 14 conveniently left in the tool box 60 during operation The chamber 12, sample intake tube assemblies 20, sample receptacles 22, and vacuum tubing 18 can be disassembled and stored in a carrying bag or back pack, along with the carrying box for the battery 16 and pump 14, for transportation to and from the sample source.

The sampling device 10 may be used with a variety of sample receptacles 22. These can vary in size, so long as they can be accommodated by the vacuum chamber 12. In addition, the user can change the material of the sample receptacle 22 (for example, from plastic to glass) depending on the nature of the liquid to be sampled, and the extent to which it might dissolve or corrode the walls of the receptacle 22.

While various implementations of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A liquid sampling device, comprising:
 a chamber, having one or more walls, for creating and sustaining a vacuum within said chamber and of sufficient size to fully enclose a sample receptacle within said chamber, said sample receptacle sized to allow positioning and support by a bottom wall of said chamber and having an opening that allows flow of air between said sample receptacle and said chamber, said chamber having a sealable door through which said sample receptacle may be placed into and removed from said chamber, a first sealable port through which air may be withdrawn to evacuate said chamber, a second sealable port through which sample liquid may be drawn for deposit into said sample receptacle when placed into said chamber, and wherein at least a portion of an inner surface of at least the bottom wall of said chamber provides an area upon which said sample receptacle may be supported and positioned when placed within said chamber;
 a means for withdrawal of air to evacuate said chamber and said sample receptacle placed within said chamber;
 a vacuum tube, having a first end slidably and releasably attached to said first port and a second end capable of releasable attachment to said means for withdrawal of air to evacuate said chamber and sample receptacle, and through which air is withdrawn from said chamber and sample receptacle when said means for withdrawal of air is activated; and a sample intake tube, having a first end for insertion into a sample source and a second end for insertion into said chamber through said second sealable port and for deposit of sample fluid into said sample receptacle, and through which air is withdrawn when said means for withdrawal of air is activated and said chamber and sample receptacle are evacuated, causing sample liquid to be drawn into said sample intake tube and thence into said chamber and sample receptacle.

2. The device of claim 1, wherein said means for withdrawal of air is a vacuum pump releasably attached to said second end of said vacuum tube.

3. The device of claim 2, wherein the length of said sample intake tube is adjusted coordinately with the power of said vacuum pump to allow collection of liquid samples from sample sources at locations distantly removed from said chamber.

4. The device of claim 2, wherein said vacuum pump is a mechanical pump.

5. The device of claim 4, further comprising a portable power supply releasably connected to said vacuum pump.

6. The device of claim 2, wherein said vacuum pump is a manually powered vacuum pump.

7. The device of claim 1, wherein the volume of said chamber is equal to or less than about three gallons, to enhance portability.

8. The device of claim 1, wherein said chamber is comprised of a material resistant to cracking or other degradation at temperatures at or below 32° F.

9. The device of claim 1, wherein said chamber is comprised of a material resistant to melting or other degradation at temperatures at or above 70° F.

10. The device of claim 1, wherein at least a portion of said chamber is comprised of a transparent material so permitting a user to observe an amount of sample collected in a sample receptacle that is at least partially transparent positioned within said chamber.

11. The device of claim 1, wherein said sample intake tube is comprised of a flexible material.

12. The device of claim 1, wherein said sample intake tube also comprises and is held to said chamber only by a resilient collar, said collar encircling at least a portion of said second end of said sample intake tube, and having a tapered end, and wherein the tapered end is correspondingly sized to said second entry port and is capable of slidable insertion into and removal from said second entry port, such that, when a vacuum is created in said chamber, said tapered end of the collar is drawn into and sealingly connects said collar and said second entry port.

13. The device of claim 12, wherein said collar is capable of slidable positioning along said sample intake tube to permit adjustment of the position of said second end within said chamber in relation to said sample receptacle.

14. The device of claim 1, wherein said second end of said sample intake tube is positioned to deposit sample liquid into a mouth of an open sample receptacle but is not fixedly attached to said receptacle.

* * * * *